United States Patent [19]

Cornish et al.

[11] Patent Number: 5,125,099
[45] Date of Patent: Jun. 23, 1992

[54] **OBTAINING HETEROPOLYSACCHARIDE-PRODUCING MICROORGANISM AND THE MICROORGANISM *AGROBACTERIUM RADIOBACTER* NCIB 40018**

[75] Inventors: Alexander Cornish, Sittingbourne; Jacqueline A. Greenwood, Leicester; John D. Linton, Sittingbourne; Colin W. Jones, Leicester, all of England

[73] Assignee: Shell Internationale Research Maatschappij B.V., The Hague, Netherlands

[21] Appl. No.: 350,978

[22] Filed: May 12, 1989

[30] Foreign Application Priority Data

May 13, 1988 [GB] United Kingdom ............... 8811365

[51] Int. Cl.$^5$ ................... C12N 1/20; C12P 19/04
[52] U.S. Cl. ..................... 435/252.2; 435/101; 435/172.1
[58] Field of Search ............ 435/172.1, 252.2, 252.3, 435/101, 245

[56] References Cited

U.S. PATENT DOCUMENTS

| | | | |
|---|---|---|---|
| 4,275,163 | 6/1981 | Gallo | 435/172.1 |
| 4,332,899 | 6/1982 | Cooney et al. | 435/172.1 |
| 4,355,103 | 10/1982 | Boguslawski et al. | 435/172.1 |
| 4,385,120 | 5/1983 | Atkinson et al. | 435/172.1 |
| 4,634,667 | 1/1987 | Linton | 435/101 |

FOREIGN PATENT DOCUMENTS 0226011 8/1985 Fed. Rep. of Germany ... 435/172.1

OTHER PUBLICATIONS

Linton, J. D. et al., "Exocellular Succinoglucan Production by *Agrobacterium radiobacter* NCIB 11883", *J. Gen. Microbiol.*, 133, pp. 2961–2969, (1987).

Williams, A. G. et al., "Exopolysaccharide Production by Pseudomona NCIB11264 Grown in Continuous Culture", *J. Gen. Microbiol.* 104, pp. 47–57, (1978).

Mian, F. A. et al., "Biosynthesis of Exopolysaccharide by *Pseudomonas aeruginosa*", *J. of Bacteriology*, 134, No. 2, pp. 418–422, (1978).

Cornish, A., et al., *Journal of General Microbiology*, 134, 3099–3110 (1988).

*Primary Examiner*—David M. Naff
*Assistant Examiner*—Marian C. Knode

[57] ABSTRACT

The invention provides a process for obtaining a second micro-organism by derivation from a first micro-organism, each micro-organism having the capability of producing an extra-cellular product when grown in the presence of a carbon-containing substrate, and the substrate uptake system of the first micro-organism being limiting for the production of the extra-cellular product, which comprises the steps of growing the first micro-organism under glucose limitation, and isolating the second micro-organism in which the glucose uptake system is at least partially derepressed, which process may further comprise the additional steps of growing the isolated second micro-organism and recovering the extra-cellular product; *Agrobacterium radiobacter* NCIB 40018, and its use for preparing a heteropolysaccharide.

3 Claims, 7 Drawing Sheets

OBTAINING HETEROPOLYSACCHARIDE-PRODUCING MICROORGANISM AND THE MICROORGANISM *AGROBACTERIUM RADIOBACTER* NCIB 40018

BACKGROUND OF THE INVENTION

The present invention relates to a process for preparing a heteropolysaccharide by cultivating a bacterium, to bacteria having the characteristic of increased heteropolysaccharide production, also to a method of producing such bacteria.

It is known that a heteropolysaccharide (in particular, a succinoglucan) can be prepared by subjecting a carbohydrate source to fermentation by certain micro-organisms such as Pseudomonas sp. NCIB 11592 as described in EP-A-0040445 (K 1480 EPC). That specification gives a full description of the use of heteropolysaccharides as a viscosifier for aqueous solutions used in oil recovery. More recently, micro-organism NCIB 11883, as described by Linton et al (1987)(this and other references by author and ear are hereinafter defined), and in EP-A-0138255 (K 1924 EPC), has been isolated; it appears to produce polysaccharide at a considerably faster rate than NCIB 11592. Further, the productivity in terms of viscosifying power as expressed by the dilution factor of the culture broth, is considerably higher in strain NCIB 11883 than in Pseudomonas sp. NCIB 11592.

It appears that most bacteria capable of growing anaerobically possess phosphotransferase systems (PTS) that catalyze the uptake and concomitant phosphorylation of glucose at the expense of phosphoenolpyruvate. By contrast, this type of glucose uptake system appears to be absent from the very limited number of aerobic bacteria in which glucose transport has been studied, although a fructose-specific PTS has been identified in *Pseudomonas aeruginosa*.

Two alternative routes for glucose uptake, both involving periplasmic proteins, have been identified in *P. aeruginosa*. During growth in continuous culture under glucose excess, oxygen-sufficient conditions this organism does not take up glucose directly but produces two periplasmic enzymes, glucose dehydrogenase and gluconate dehydrogenase, that sequentially oxidise glucose to gluconate and 2-ketogluconate which are then taken up via specific transport systems (Midgley and Dawes, 1973; Roberts et al, 1973; Whiting et al, 1973). This extracellular oxidation system is repressed during glucose-limited growth (Whiting et al, 1976), and glucose is taken up directly via a high-affinity transport system (Midgley and Dawes, 1973). The latter involves a periplasmic, glucose-binding protein (Stinson et al, 1977), and thus appears to be analogous to the binding protein-dependent transport systems for certain sugars, amino-acids and inorganic ions that have been investigated in detail in enteric bacteria (Ames, 1986).

*Agrobacterium radiobacter* NCIB 11883, the recently-isolated aerobic bacterium of industrial importance, is unable to metabolize glucose using the indirect, oxidative route since it produces a non-functional, apoenzyme form of glucose dehydrogenase that lacks the PQQ (pyrroloquinoline quinone) co-factor (Linton et al, 1986; Cornish et al, 1987).

SUMMARY OF THE INVENTION

The present invention is based on the specific discovery of a micro-organism which produces heteropolysaccharide from glucose at a faster rate even than NCIB 11883, by derivation from that known organism, and to a general procedure for obtaining organisms which, by comparison with parent organisms from which they are derived, exhibit improved polysaccharide or other extra-cellular material production.

A process according to the present invention derives a second micro-organism from a first micro-organism, each micro-organism having the capability of producing an extra-cellular product when grown in the presence of a carbon-containing substrate, and the substrate uptake system of the first micro-organism being limiting for the production of the extra-cellular product, the process comprising the steps of growing the first micro-organism under substrate limitation, and isolating the second micro-organism in which the substrate uptake system is at least partially derepressed. By growing the isolated second micro-organism, preferably under nitrogen limitation the extra-cellular product can be recovered. The extra-cellular product is, for example, a heteropolysaccharide, e.g. a heteropolysaccharide comprising glucose and, for each 7 moles of glucose, 0.9–1.2 moles of galactose, and 0.65 to 1.1 moles of pyruvate, together with succinate and acetate in molar proportions (based on 7 moles of glucose) between 0 and 2, and the carbon substrate may be glucose.

The present invention follows investigation of the mechanism via which A. radiobacter takes up glucose directly during growth in glucose-limited continuous culture.

When NCIB 11883 was grown in glucose-limited continuous culture at low dilution rate, whole cells transported glucose using an energy-dependent mechanism which exhibited an accumulation ratio >2000. Three periplasmic proteins, which together constituted up to approximately 45% of the total cell protein, were purified. Two of these, identified herein as GBP1 ($M_r$ 36500) and GBP2 ($M_r$ 33500), bound D-glucose with high affinity ($K_D$ 0.23 and 0.07 M respectively), whereas the third protein (Mr 30500) showed no binding ability. (GBP=glucose-binding protein). Competition experiments using various analogues showed that those which differed from glucose at C-6 (e.g. 6-chloro-6-deoxy-D-glucose and 6-deoxy-D-glucose) variably decreased the binding of glucose to both GBP1 and GBP2, whereas those which differed at C-4 (e.g. D-galactose) were only effective with GBP2. The rate of glucose uptake and the concentration of the glucose-binding proteins increased in parallel during prolonged growth under glucose-limitation due to the emergence of new strains, identified herein as AR18 and AR9, in which the synthesis of GBP1 or GBP2, but not both, was respectively further derepressed. Apparently, therefore, *A. radiobacter* synthesizes two distinct periplasmic binding proteins which are involved in glucose transport and which are maximally derepressed during growth under glucose limitation. A strain corresponding closely to strain AR18 has also been produced during growth of NCIB 11883 in a galactose-limited continuous culture at similar low dilution rate.

The newly-emerged strains have been isolated. AR18 has been deposited under the provisions of the Budapest Treaty on the International Recognition of the Deposit of Microorganisms for the Purposes of Patent Procedure on May 6, 1988 at the National Collections of Industrial & Marine Bacteria Ltd., Torry Research Station, 135 Abbey Road, Aberdeen, AB9 8DG, Scotland and has been assigned accession number NCIB 40018.

AR18 contains an increased effective concentration of GBP1 and provides increased heteropolysaccharide (specifically, succinoglucan) production with respect to NCIB 11883, e.g. when grown with glucose as the carbon source, either in ammonia-limited continuous culture at low dilution rate or in batch culture on ammonia exhaustion. The invention therefore specifically provides *Agrobacterium radiobacter* NCIB 40018 and its use for preparing a heteropolysaccharide. Glucose uptake by strain AR18 was significantly less repressed during ammonia limitation than when growing either the original parent strain or strain AR9, under the same conditions, and this was reflected both in its relatively high concentration of GBP1 and in its significantly higher rate of succinoglucan synthesis. Flux control analysis using 6-chloro-6-deoxy-D-glucose as an inhibitor of glucose transport showed that the latter was a major kinetic control point for succinoglucan production. It appears, therefore, that glucose uptake by *A. radiobacter*, particularly via the GBP1-dependent system, is only partially repressed during ammonia-limited growth, and that the organism avoids the potentially deleterious effects of accumulating excess glucose by converting the surplus into succinoglucan.

AR18 contains up to 30% GBP1, as a percentage of the total cell protein; the GBP1 content of the parent organism is about 5%. These are values under glucose limitation. GBP2, apparently the second glucose uptake-limiting binding protein in NCIB 11883, has effectively been repressed in AR18.

It is likely that other substrate uptake systems containing two substrate-binding proteins can be modified in the same way, in any suitable species. Prolonged substrate-limited growth may also be expected to derepress other substrate uptake systems, in accordance with the invention. These procedures, as in the particular example of NCIB 11883 - AR18, are both reproducible and at least partially reversible.

The extra-cellular product of a micro-organism modified in accordance with the invention may comprise a succinoglucan heteropolysaccharide comprising glucose and, for each 7 moles of glucose, 0.9-1.2 moles of galactose, and 0.65 to 1.1 moles of pyruvate, together with succinate and acetate in molar proportions (based on 7 moles of glucose) between 0 and 2. Such succinoglucan heteropolysaccharides are described in EP-A-0040445. For this purpose, the micro-organism is grown in aqueous nutrient medium by aerobic cultivation. The procedure may suitably be carried out as a batch-process, a fed-batch process with or without fill and draw or as a continuous process. From productivity considerations, a continuous process or a fill and draw process is preferred.

Preferably, the organism is grown in the absence of yeast extract in a chemically-defined medium. More preferably the process is carried out under non-carbon source nutrient limitation conditions, e.g. nitrogen limitation or exhaustion. The use of a chemically defined medium is advantageous since, for a given productivity or for a given final cell concentration, it appears to be easier to handle a nitrogen source such as sodium glutamate, ammonium or nitrate salts than to handle complex nitrogen sources such as yeast extract or distillers' dried solubles The nitrogen source is preferably selected from the group consisting of sodium glutamate, ammonium sulphate and sodium nitrate.

The present invention further relates to the heteropolysaccharide as prepared by the process as described above, and to the use of the heteropolysaccharide as viscosity modifier in an aqueous solution. The present invention also relates to an aqueous system whenever thickened by the present heteropolysaccharide. Preferably the aqueous system belongs to the group consisting of completion fluids, work-over fluids, stimulation fluids and drilling fluids. Stimulation fluids are used for, e.g. hydraulic fracturing and acid fracturing. Most completion, work-over, drilling and stimulation fluids contain at least one other additive, e.g. salts (such as may be present in all brines), fluid loss additives, clay stabilizers, acids, bases, surfactants etc. The aqueous systems to be thickened can however also be a printing ink or even a French dressing.

A drilling fluid comprising water and 0.06–1.5% by weight of the above heteropolysaccharide is a further preferred embodiment of the present invention. The present invention also encompasses a method of treating a well comprising the introduction into the well of an aqueous medium comprising water and 0.05–1.5% by weight of the above heteropolysaccharide. The aqueous medium is suitably a brine and may contain additives as desired.

The present invention further provides the use in enhanced oil recovery (EOR) of an aqueous solution comprising the above heteropolysaccharide. Use in EOR can be for displacing a fluid through a well and/or a permeable subsurface formation communicating with the well, in mobility control as mobility buffer, e.g. in surfactant micellar flooding, use in profile control, to reduce water production, to reduce water/oil ratio etc.

In general, the present invention provides the ability to amplify known production rates of extra-cellular material. The ability to identify and drepress a limiting factor gives rise to the option of isolating the gene for an essentially non-limiting, but normally-repressed substrate-binding protein, or of a part of the genome associated with its synthesis, and cloning it into a suitable host via which the desired product can be made.

The following experimental procedures illustrate the invention, together with the accompanying drawings.

DETAILED DESCRIPTION

METHODS (1)

Figures 1A, 1B, 1C:
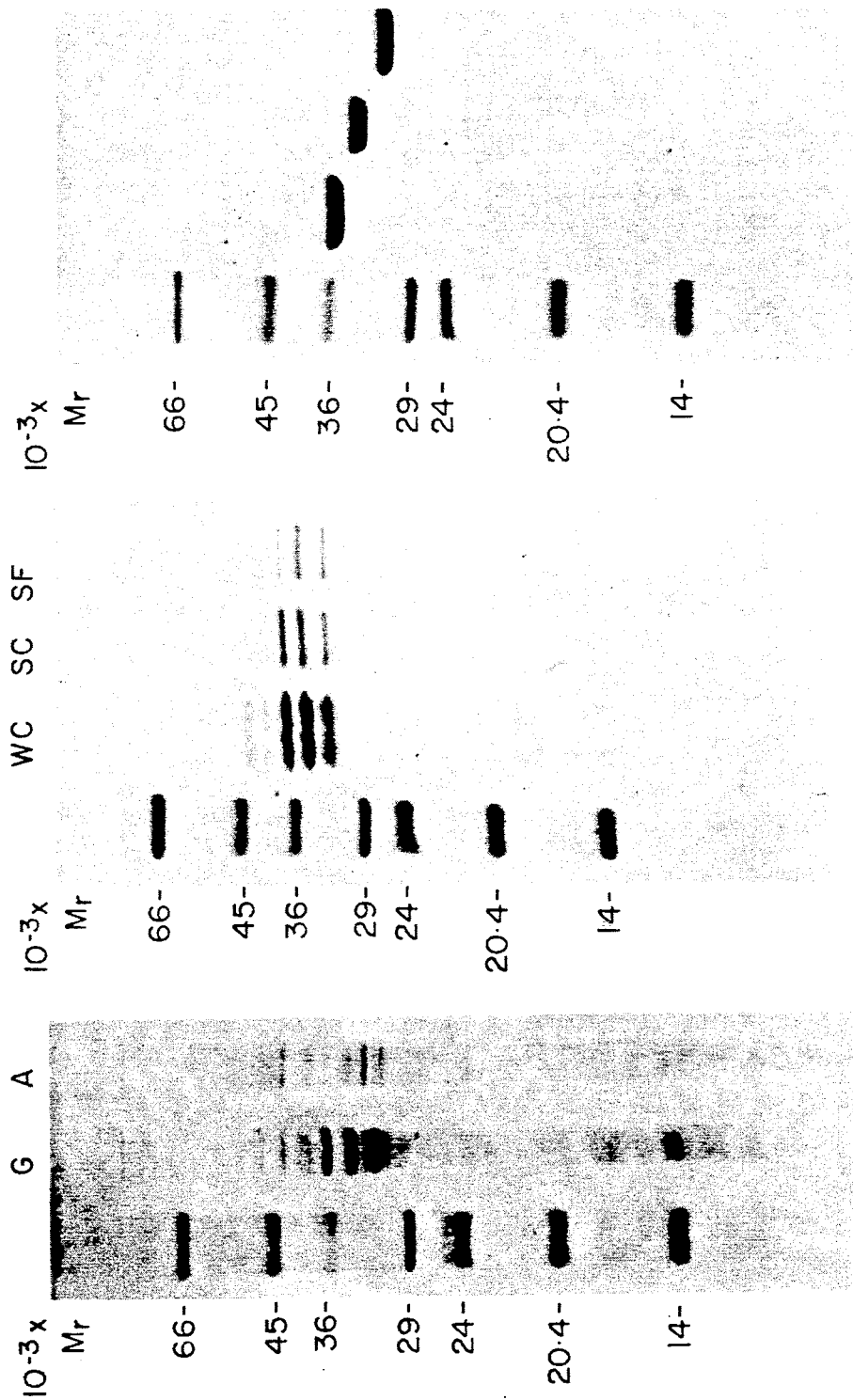
FIGS. 1A, 1B and 1C illustrate results of purification of proteins from whole cells of *A. radiobacter*.

Organism and growth conditions. *Agrobacterium radiobacter* NCIB 11883 was grown at 30° C. in continuous culture (D=0.045 h$^{-1}$) under glucose limitation using a chemically defined medium (Linton et al., 1987) supplemented with glucose (4 gl$^{-1}$), ammonium sulfate (3 gl$^{-1}$) and nitrilotriacetic acid (0.142 gl$^{-1}$). The organism was grown in an LH Series 500 chemostat of 2 l working volume at a steady-state biomass density of 2.1 g dry wt l$^{-1}$.

Preparation of cell suspensions. Cell suspensions were prepared using 20 mM HEPES buffer, pH 7.0, as described by Cornish et al., 1987.

Measurement of glucose uptake. Rates of glucose uptake were determined by measuring the incorporation of D-[U-$^{14}$C]glucose into whole cells over a period of 60 s. Assays were carried out in an open-topped Rank oxygen electrode vessel containing 1 ml 20 mM HEPES/KOH buffer, pH 7.0, and 1 mg dry wt cells. The contents of the vessel were maintained at 30° C. and mixed continuously using a magnetic stirrer. Assays were started by adding D-[U-$^{14}$C]glucose [2 mCi mmol$^{-1}$ (74 MBq mmol$^{-1}$; 0.5 uCi (18.5 KBl)] to give a final concentration of 250 uM. Samples (50 ul) of the reaction mixture were withdrawn at 15 s intervals and the cells were collected on nitrocellulose filters of 0.45 uM pore size (2.5 cm dia.; Sartorius) by means of a manifold connected to a vacuum line. The filters were washed immediately using 3 ml 20 mM HEPES, pH 7.0, dried under an infra-red lamp and then immersed in 3 ml of Fisofluor 3 scintillant (Fisons Ltd.). The extent of incorporation of [$^{14}$C]glucose into the cells was determined by counting the radioactivity on the filters using a Hewlett Packard Tri-Carb liquid scintillation counter (80-85% efficiency). Glucose uptake rates were measured in triplicate for each batch of cells and the standard errors never exceeded 10% of the mean values.

In order to measure glucose uptake rates at low concentrations of substrate (1-5 uM) the cell density was reduced to 0.01 mg ml$^{-1}$, the specific activity of the [$^{14}$C]glucose was increased to 84 mCi mmol$^{-1}$ (3.2 Gbq mmol$^{-1}$) and the rate of incorporation of $^{14}$C-label into cells was measured over a period of 35 s. These modifications ensured that less than 20% of the glucose was consumed during the incubation.

The capacity of *A. radiobacter* to accumulate glucose was determined by incubating cell suspensions (1 mg dry wt ml$^{-1}$) with D-[U-$^{14}$C]glucose [84 mCi mmol$^{-1}$ (3.2 Gbq mmol$^{-1}$); 20M initial concentration). Samples (100 ul) of the suspension were withdrawn 10s after adding the glucose and the cells were collected on nitrocellulose filters (0.45 um pore size) using vacuum filtration. The filters were washed immediately using 3 ml buffer and immersed in 20 ml boiling water. Aqueous extracts prepared from four filters were pooled, lyophilized and the residue dissolved in 2 ml water. The glucose content of the cells was determined using liquid scintillation counting following separation of [$^{14}$C]glucose from other labelled metabolites present in the extracts using paper chromatography. Samples of the filtrate plus washings were also counted in order to determine the extracellular concentration of glucose at the time of sampling.

The substrate specificity of the transport system was investigated by determining the extent to which unlabelled glucose analogues (10 mM) reduced the rate of uptake of [$^{14}$C]glucose (250 uM). Cell suspensions were incubated with analogues for 5 s prior to addition of [$^{14}$C]glucose. Where indicated, carbonyl cyanide p-trifluoromethoxyphenylhydrazone (FCCP) (2 ul of a 10 mM stock solution in dimethylformamide) was added to the cell suspension 10 s before the glucose; uptake was not affected by the presence of the solvent alone.

Osmotic shock. This was done essentially as described by Neu and Heppel (1965) except that plasmolyzed cells were shocked using ice-cold 20 mM bis-Tris buffer, pH 6.8, instead of distilled water.

FPLC. Periplasmic proteins released by osmotic shock were separated using anion-exchange fast protein liquid chromatography (FPLC). Samples of shock-fluid (10-15 ml containing 5-10mg protein) were passed through an acrodisc filter of 0.45 um pore-size filter (Gelman Ltd.) in order to remove particulate material, and the filtrate was loaded onto a Mono-Q column (Pharmacia) equilibrated with 20 mM bis-Tris, pH 6.8. All of the periplasmic proteins bound to the column under these conditions and were eluted in turn using a linear KCl gradient (the KCl concentration was increased from 0-200 mM over 20 minuntes using a flow rate of 1 ml min$^{-1}$). The protein content of the effluent was monitored at 280nm. The three most abundant periplasmic proteins ($M_r$=36500, 33500 & 30500, which were eluted using 140 mM, 60 mM and 90 mM KCl respectively) were virtually homogeneous after this purification step (>95% pure as judged by SDS-PAGE analysis) and were stored at −20° C. until required.

Gel-filtration FPLC was used to estimate the sizes of the purified proteins. Samples of pure proteins (200 ul, containing approximately 200 ug protein) were loaded onto a Superose 12 column (Pharmacia) equilibrated with 20 mM bis-Tris, pH 6.8, and were eluted using a flow rate of 0.3 ml min$^{-1}$. The protein content of the effluent was monitored at 280 nm and the retention time for each protein was noted. The column was calibrated using a mixture of the following proteins ($M_r$ values given in parentheses): bovine albumin, 132000 (dimer) and 66000 (monomer); egg albumin, 45000; carbonic anhydrase, 29000; and horse-heart cytochrome c, 12400).

SDS-PAGE. Discontinuous electrophoresis of proteins was carried out using 12% (w/v) acrylamide gels according to the method of Laemmli (1970). Whole cells of *A. radiobacter* were boiled for 4 min in dissolving buffer (Laemmli, 1970) and a volume containing 20 g protein was loaded into each gel track. The gels were stained for protein with Kenacid Blue R (Weber & Osborn, 1975), then destained and scanned at 633nm using an LKB laser densitometer linked to a recording integrator. The following proteins were used as molecular weight standards ($M_r$ values given in parentheses): alpha-lactalbumin, 14200; trypsin inhibitor, 20100; trypsinogen, 24000; carbonic anhydrase, 29000; glyceraldehyde-3-phosphate dehydrogenase, 36000; egg albumin, 45000; and bovine albumin, 66000).

Determination of binding constants using equilibrium dialysis. This was carried out at 4° C. using an eight-cell rotating module (Hoefer Scientific Instruments, San Fransisco, Calif., U.S.A.). Each cell was divided into two chambers of 0.5 ml volume using a dialysis membrane (Mr cut-off=6-8000). Pure protein (0.5 nmol) was added to one chamber of each cell in 0.3 ml bis-Tris, pH 6.8. Each of the opposing chambers was loaded with 0.3 ml bis-Tris (0.3 ml) containing D-[U-

$^{14}$C]glucose [270 mCi mmol$^{-1}$ (10 GBq mmol$^{-1}$)], the concentration of which was varied over an appropriate range. The module was rotated at 10 rev min$^{-1}$ for 30 h (by which time equilibrium had been attained) and samples (50 ul) were taken in triplicate from each chamber and counted in 3 ml Fisofluor 2 (Fisons Ltd.). The data were analyzed according to the method of Scatchard (1949).

The capacity of glucose analogues to reduce the extent of binding of D-[U-$^{14}$C]glucose to pure proteins was determined by modifying the assay procedure as follows. One chamber of each cell contained 0.5 nmol pure protein in 0.3 ml bis-Tris, pH 6.8, and the other chamber was loaded with 0.3 ml of buffer containing 3 nmol D-[U-$^{14}$C]glucose [85 mCi mmol$^{-1}$ (3.2 GBq mmol )] plus 120 nmol of an unlabelled glucose analogue. The quantity of [$^{14}$C]glucose that bound to the proteins in the presence and absence of unlabelled glucose analogues was determined after 30 h incubation.

Pulse labelling. L-[$^{35}$S]methionine [>800 Ci mmol$^{-1}$ (30 TBq mmol$^{-1}$); 50 uCi (1.85 MBq)] was added to a logarithmic phase culture (50 ml) of *A. radiobacter*, followed 10 min later by unlabelled methionine (1 mM). Samples (1.5 ml) were taken at 0.5 h intervals for 5 h, then immediately centrifuged, washed and resuspended in dissolving buffer (Laemmli, 1970) prior to boiling for 4 min. After SDS-PAGE, radiolabelling of major proteins was determined by autoradiography or by scintillation counting of excised bands (Quilter & Jones, 1984).

Enzyme assays. 6-Phosphogluconate dehydrogenase activity was assayed as using the method of Beardsmore et al. (1982).

Presentation of data. Where appropriate, values have been given as the mean ±SEM with the number of independent determinations in parentheses.

Chemicals. D-[U-$^{14}$C]Glucose [270 mCi mmol$^{-1}$ (10 GBq mmol$^{-1}$)] and L-[$^{35}$S]methionine [>800 Ci mmol$^{-1}$ (30 TBq mmol$^{-1}$)] was purchased from Amersham. Glucose analogues were obtained from Sigma. Other reagents were purchased from Fisons Ltd. and were of the highest grade available.

RESULTS (1)

Whole cell studies on the mechanism of glucose uptake by *A. radiobacter* following growth in continuous culture under glucose limitation at a dilution rate of 0.045 h$^{-1}$ The rates of glucose uptake measured for five independent glucose-limited cultures yielded a mean value of 55±3 nmol min$^{-1}$ (mg dry wt)$^{-1}$, identical to the value determined for the rate of glucose uptake in situ at $u_{max}$ (0.35 h$^{-1}$) and considerably greater than the in situ rate of glucose utilisation at D=0.045 h$^{-1}$ [9 nmol min$^{-1}$ (mg dry wt)$^{-1}$] (Linton et al., 1987). Beyond the first 60 s after adding [$^{14}$C glucose to the cell suspensions, the uptake rate decreased abruptly to a value of approximately 40 nmol min$^{-1}$ (mg dry wt) and probably reflected the rate at which glucose was further metabolized rather than the potential activity of the transport system per se. Glucose uptake rates did not increase when cell suspensions were pre-incubated with respiratory substrates (e.g. 10 mM ethanol or 10 mM glycerol) prior to the addition of [$^{14}$C]glucose, indicating that the oxidation of endogenous substrate (Cornish et al., 1987) provided sufficient energy to support the maximum rate of glucose transport.

For many bacterial sugar transport systems it has proved possible to isolate transport activity from subsequent metabolism, thus enabling the kinetic constants and other important parameters of the uptake system to be determined. This has been accomplished either by measuring the capacity of whole cells to accumulate non-metabolizable, radiolabelled analogues of a naturally-occuring sugar or by using mutants that are unable to metabolize a given sugar but retain the relevant transport system (see Henderson, 1986). It was not appropriate in the current work to study glucose transport using mutants of *A. radiobacter* defective in glucose metabolism since the primary objective was to identify the mode of transport used during growth under glucose limitation. The possibility of using radiolabelled alpha-1-O-methyl-D-glucose, 3-O-methyl-D-glucose or 2-deoxy-D-glucose (which are the only non-metabolizable, radiolabelled analogues of glucose available from commercial sources) as artificial substrates of the glucose uptake system(s) was considered but, unfortunately, none of these unlabelled analogues appreciably reduced the rate of [$^{14}$C]glucose uptake by *A. radiobacter* when they were added at a 40:1 molar excess, thus indicating that the organism displays a large preference for the natural substrate (see below).

The assay system used to measure the rate of glucose uptake undoubtedly underestimated the actual rate of transport since some of the [$^{14}$C]glucose taken up by the cells would have been oxidized to $^{14}CO_2$. This was confirmed by immediately immersing the filters in scintillant (see Henderson, 1986), rather than allowing them to dry under the infra-red lamp; under these conditions the observed rate of glucose uptake was increased by 25%.

Accurate determination of the kinetic parameters (i.e. $K_m$ and $V_{max}$) for glucose transport by *A. radiobacter* was not possible in the presence of further metabolism. However, the rate of glucose uptake did not change when the concentration of [$^{14}$C]glucose used in the assay system was varied over the range 1 M-1 mM, indicating that the $K_m$ for glucose uptake less than 1 M.

Glucose transport was strongly inhibited by the uncoupling agent FCCP (approximately 95% inhibition at 20 M). Unmodified glucose accounted for 70% of the total radioactivity recovered when cells were incubated with [$^{14}$C] glucose for 10 s before being washed rapidly and extracted in boiling water, and an accumulation ratio ([glucose]$_{in}$/[glucose]$_{out}$) of 2000-6000 was estimated by assuming an intracellular volume of 1-3 ul mg dry wt$^{-1}$. These results indicated that the organism was capable of taking up glucose actively against a large concentration gradient using a non-phosphotransferase system (since in the latter case the uptake and phosphorylation of glucose would have taken place concomitantly (Postma, 1986)). A proton symport mechanism was also ruled out since there was no evidence of any alkalinization when glucose was added to suspensions of *A. radiobacter* under strictly anaerobic conditions using the method of Henderson and Macpherson (1986). The possibility was therefore considered that glucose was being taken up by a system involving a periplasmic binding protein. Binding protein-dependent transport systems in enteric bacteria have often been reported to be highly susceptible to osmotic shock procedures that cause the substrate-binding protein to be released from the periplasm, but relatively resistant to inhibition by uncouplers (a variety of evidence suggests that such systems are driven by ATP hydrolysis rather than by the protonmotive force per se, but the mechanism of energy coupling has not been determined unequivocally; see Ames, 1986). The finding that FCCP was a powerful inhibitor of glucose transport in *A. radiobacter* was therefore perfectly compatible with the possibility that a periplasmic binding protein was involved, since an aerobic organism of this type probably depends largely on oxidative phosphorylation rather than substrate-level phosphorylation to produce ATP. In order to confirm the involvement of a binding protein system it was decided to investigate whether *A. radiobacter* did indeed contain periplasmic, glucose-binding proteins during growth under glucose limitation.

Characterization of periplasmic glucose-binding proteins isolated from *A. radiobacter* following growth under glucose limitation As the glucose uptake rates of whole cells of *A. radiobacter* which had been grown under glucose limitation (D=0.045 h$^{-1}$) were comparable to the glucose uptake rate at u$_{max}$, it was concluded that the glucose uptake system was substantially de-repressed so as to enable the organism to take up glucose at the in situ rate of 9 nmol min$^{-1}$ (mg dry wt)$^{-1}$, even when the standing concentration of glucose in the chemostat was very low. These observations suggested that it might be possible to identify components of the glucose transport system by using SDS-PAGE to compare the polypeptide profiles of cells which had been grown under different nutrient limitations, the expectation being that any transport proteins would be maximally de-repressed only during glucose-limited growth. Using this approach it was found that *A. radiobacter* produces three proteins (M$_r$ values = 36500, 33500 and 30500 as judged by SDS-PAGE) at high concentrations, in response to glucose limitation (FIG. 1A). Furthermore, all three proteins were partially released from the cells by osmotic shock (FIG. 1B), and this was accompanied by a decrease of approximately 30% in the rate of glucose intake. As this treatment did not appear to damage the cytoplasmic membrane to any extent, since 6-phosphogluconate dehydrogenase was not detected in the shock fluid, it was concluded that all three proteins were located in the periplasm. The three proteins were purified to near homogeneity from the shock fluid using anion exchange FPLC (FIG. 1C), and their sizes were estimated using gel filtration FPLC (M$_r$=44000, 38000 and 36000). These values, which were slightly higher than the estimates obtained using SDS-PAGE, suggest that all three proteins exist as monomers.

Figure 2:
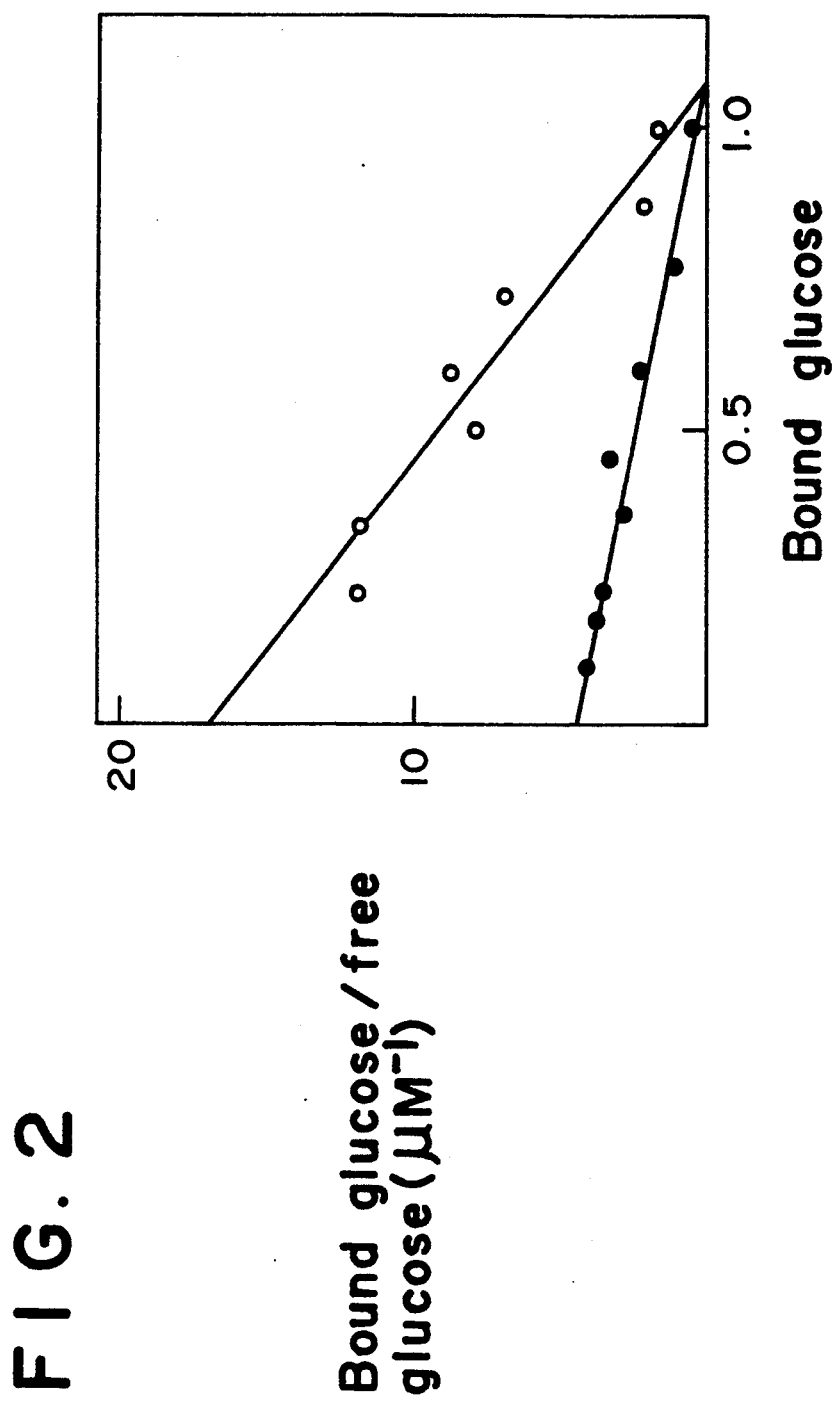
FIG. 2 is a graph (Scatchard plots) relating to binding of glucose to two proteins released from whole cells of *A. radiobacter* by osmotic shock.

Equilibrium dialysis showed that only the larger two proteins were able to bind glucose and these are referred to hereafter as GBP1 (M$_r$=36500) and GBP2 (M$_r$=33500). Binding isotherms indicated that both proteins contained a single glucose binding site, but GBP2 (K$_D$=0.07 uM) displayed a considerably higher affinity for glucose than GBP1 (K$_D$=0.23 uM) (FIG. 2). Competitive binding assays revealed that GBP1 and GBP2 also differed in their capacity to discriminate betwen certain glucose analogues (Table 1). Alpha-1-O-methyl-D-glucose, 3-O-methyl-D-glucose and 2-deoxy-D-glucose did not affect the binding of glucose to either GBP1 or GBP2 and also failed to reduce significantly the rate of glucose uptake by whole cells of *A. radiobacter* (see above). By contrast, analogues which differed from glucose in having alternative substituents at C-6 (i.e. 6-deoxy-D-glucose and 6-chloro-6-deoxy-D-glucose), or in lacking C-6 altogether (i.e. D-xylose), significantly reduced the amount of [$^{14}$C]glucose that bound to both GBP1 and GBP2. However, 6-deoxy-D-glucose and D-xylose were much more effective with GBP2 than GBP1, whereas the converse was found to be the case for 6-chloro-6-deoxy-D-glucose. D-Galactose and D-fucose (6-deoxy-D-galactose) were only effective with GBP1, thus indicating that the configuration at C-4 is important in determining whether a sugar can compete effectively with glucose for GBP2. The function of the third periplasmic protein (M$_r$=30500) is as yet unclear. However, it seems likely that it is also a periplasmic substrate-binding protein, and for the purpose of this work it will be referred to as BP3.

Figure 3:
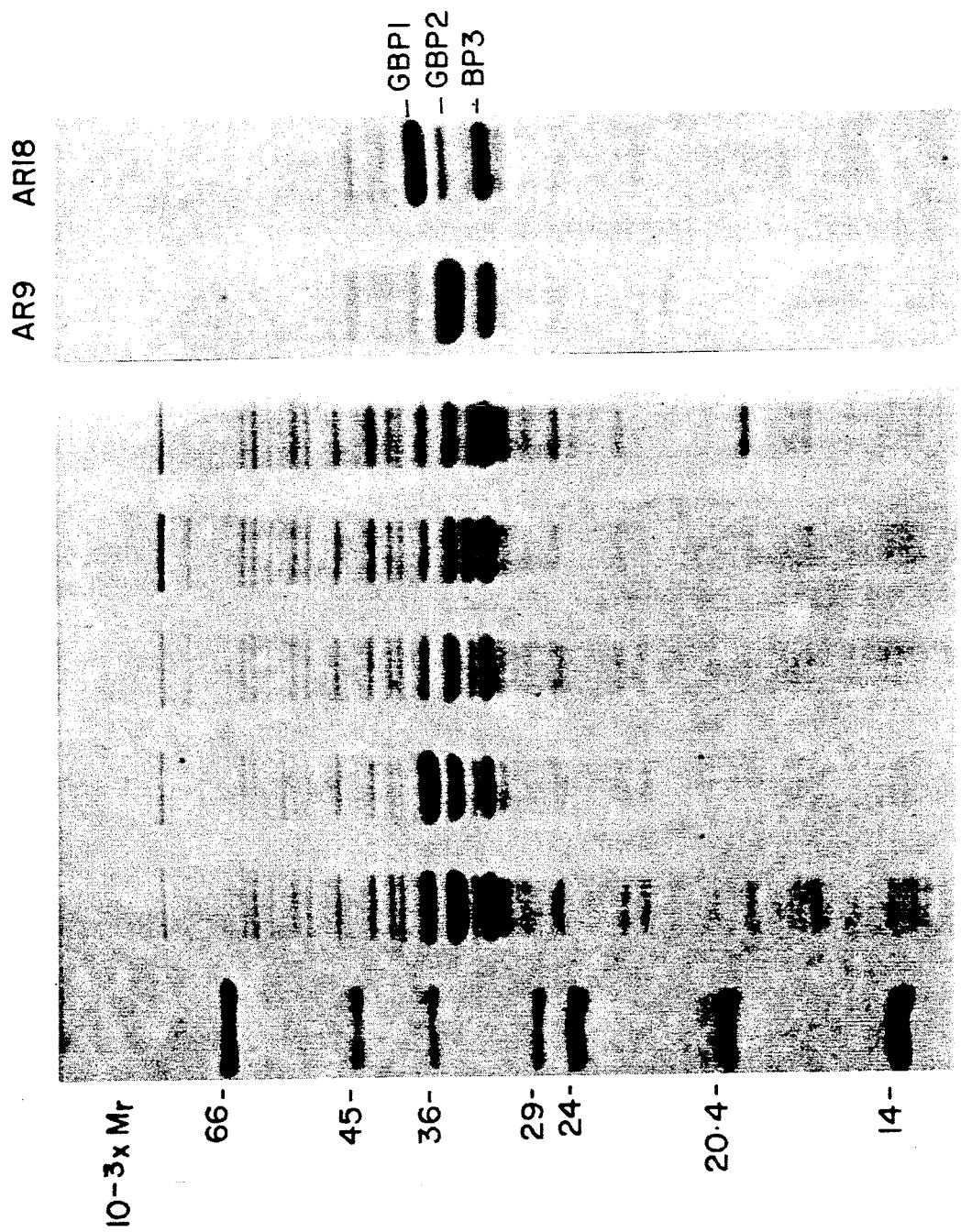
FIG. 3 shows variations in concentrations of GBP1, GBP2 and BP3 in cells of *A. radiobacter* from several different cultures grown under glucose limitation.
Figure 4:
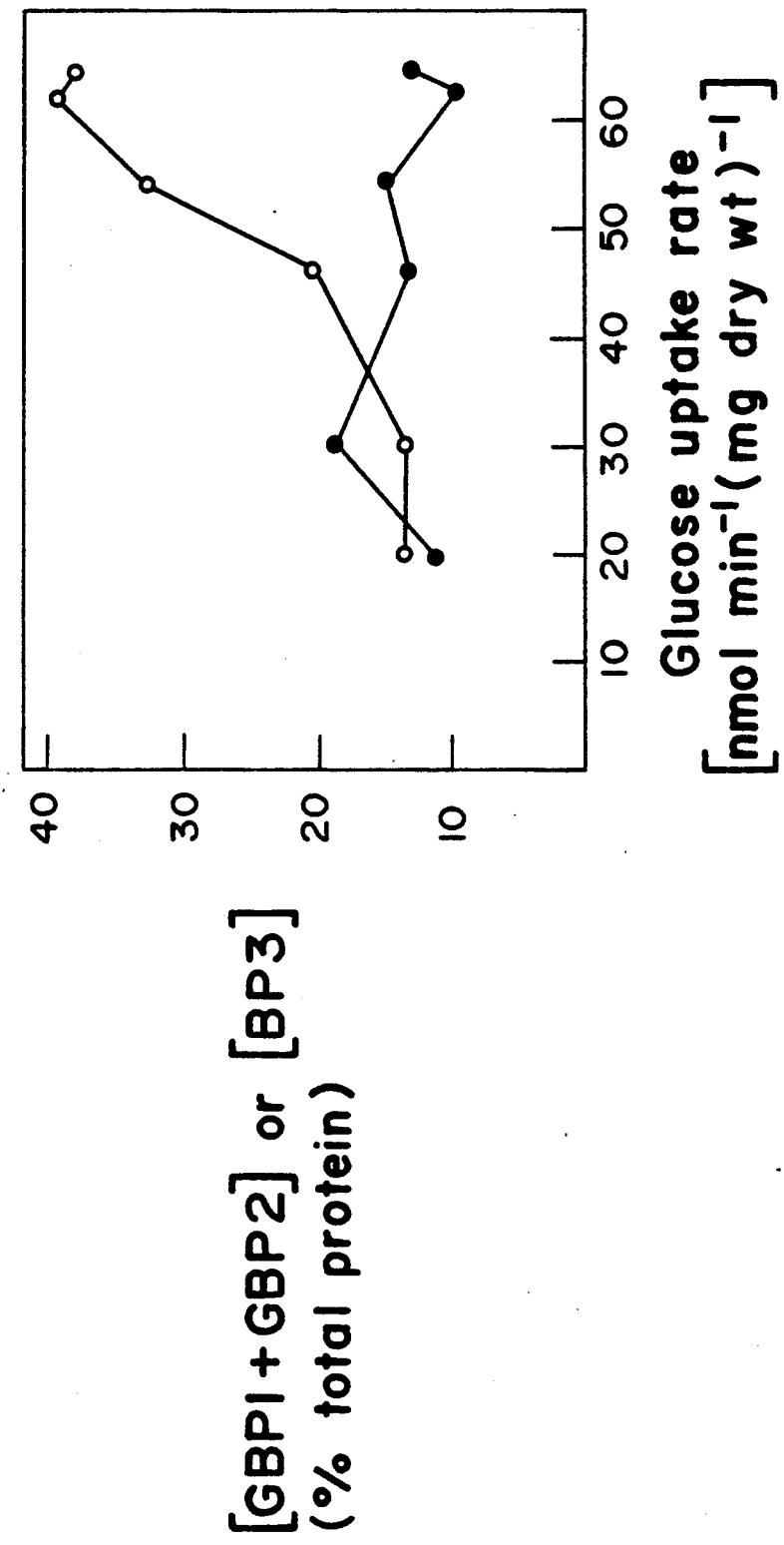
FIG. 4 is a graph of relationship of glucose uptake capacity with concentration of GBP1, GBP2 and BP3.

Variations in the concentrations of periplasmic glucose-binding proteins during growth of *A. radiobacter* in continuous culture under glucose limitation at a dilution rate of 0.045 h$^{-1}$ The glucose uptake rates of approximately 55 nmol min$^{-1}$ (mg dry wt)$^{-1}$ reported above for whole cells of *A. radiobacter* grown under glucose limitation (D=0.045 h$^{-1}$) were for cultures that had been grown under these conditions for at least 20 generations. It was subsequently found that cultures which had been grown under glucose limitation for shorter periods (<10 generations) sometimes exhibited glucose uptake rates as low as 20 nmol min$^{-1}$ (mg dry wt)$^{-1}$. When the polypeptide profiles of cells having different glucose uptake rates were compared using SDS-PAGE it was found that both the absolute and relative concentrations of GBP1 and GBP2 varied significantly between different cultures, but the concentration of BP3 remained relatively constant (FIG. 3). Furthermore, there was a clear correlation between the glucose uptake rates of cells from different glucose-limited cultures and the total concentration of GBP1 plus GBP2, but not BP3 (FIG. 4). This relationship confirmed that GBP1 and GBP2 both played a role in the uptake of glucose by *A. radiobacter* during growth in continuous culture under glucose limitation, although at this stage it was not clear why the organism produced two distinct glucose-binding proteins, the levels of expression of which varied between different cultures.

Figure 5:
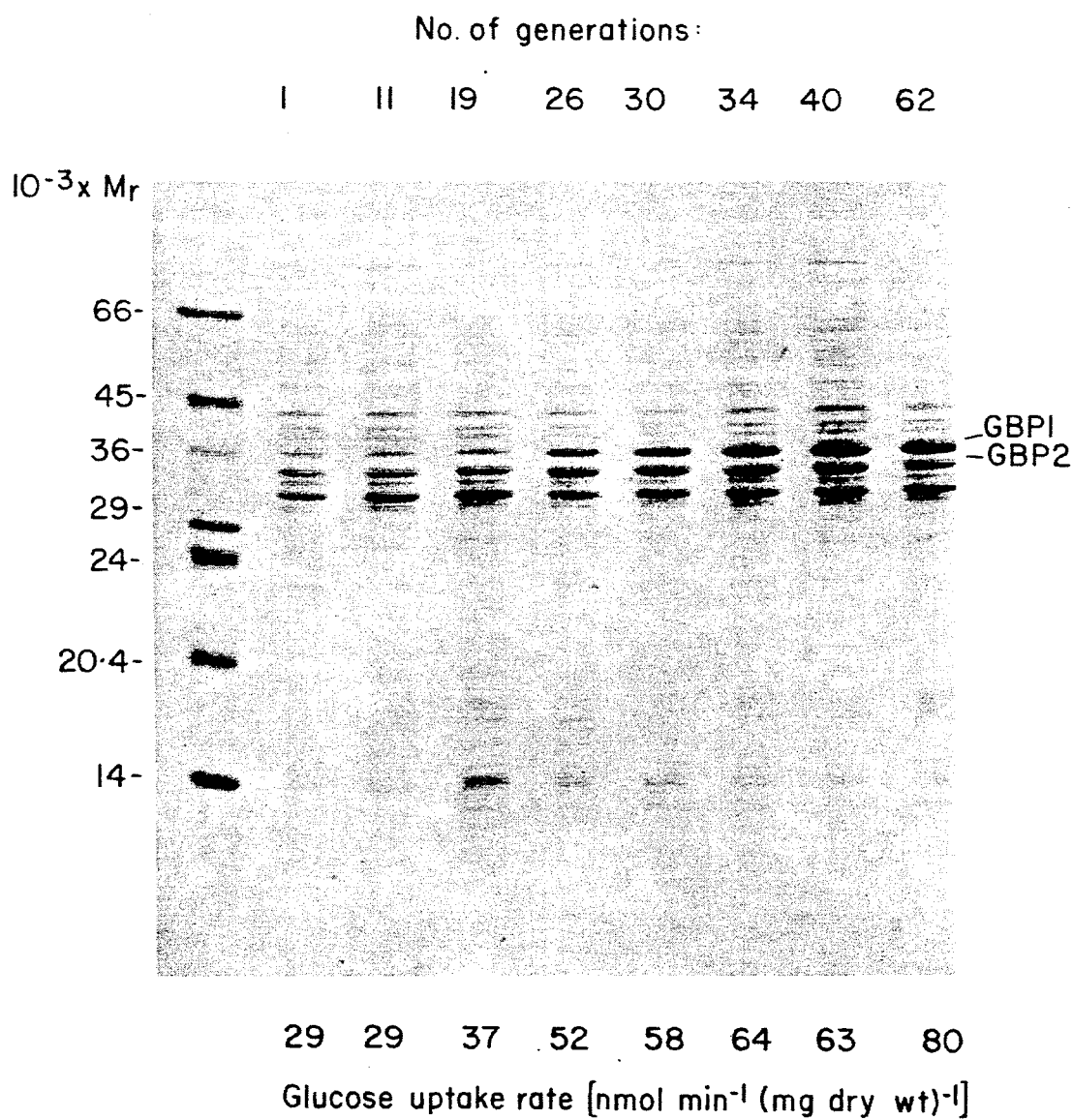
FIG. 5 shows changes in concentrations of GBP1 and GBP2 after prolonged growth of *A. radiobacter* under glucose limitation.

It was subsequently noted, however, that the concentrations of both GBP1 and GBP2 (but not BP3) both increased when the organism was grown in continuous culture under glucose limitation over a long period, but GBP1 eventually predominated (FIG. 5). This observation suggested that the selective pressures imposed during an extended period of glucose-limited growth (i.e. during growth at extremely low ambient concentrations of glucose) favored the growth of strains of *A. radiobacter* that contained higher concentrations of the two glucose binding proteins than were present in the parent organism and were therefore capable of taking up glucose at higher rates in situ.

Figure 6:
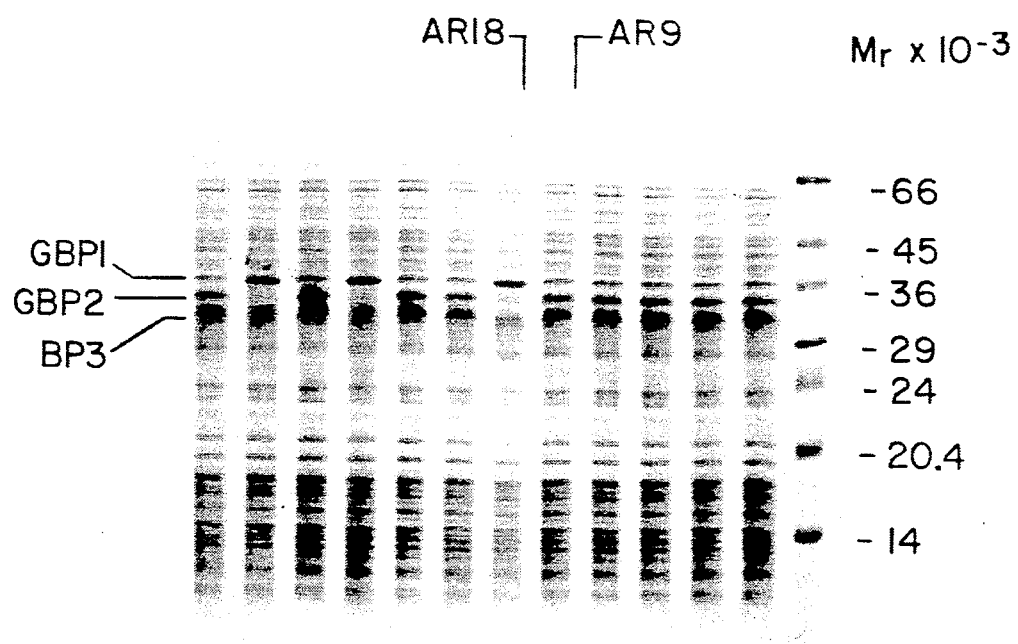
FIG. 6 illustrates strains of *A. radiobacter* having different concentrations of glucose-binding proteins.

Isolation and Characterization of Different Strains of *A. radiobacter* Selected During Growth Under Glucose Limitation In order to investigate whether transport systems involving the two glucose-binding proteins were becoming de-repressed simultaneously throughout the entire bacterial population in the chemostat, a sample was withdrawn from a glucose-limited culture that was fully derepressed with respect to glucose uptake (64 nmol min$^{-1}$ (mg dry wt)$^{-1}$, and the cells were plated out on a solid medium containing glucose as sole carbon source. Twenty three colonies were then picked at random and used to inoculate vials containing 3 ml of glucose-minimal medium. The cultures were grown at 30° C. at $u_{max}$ until the glucose was exhausted (final cell density=0.5 mg dry wt ml$^{-1}$), after which time the polypeptide profiles of the cells were examined using SDS-PAGE. Two distinct phenotypes could be distinguished based on the relative concentrations of GBP1, GBP2 and BP3. Cells originating from 11 of the colonies contained predominantly GBP1, whilst GBP2 and BP3 were the most abundant in cells derived from the remaining colonies, although GBP1 was still discernible (FIG. 6). The phenotypes appeared to be stable as no change in the protein profiles was observed when individual isolates were subjected to two further rounds of colony selection followed by growth in liquid culture. These observations suggested that *A. radiobacter* responded to prolonged growth under glucose limitation by segregating into different populations in which GBP1 and GBP2 were differentially expressed.

Two isolates representative of the different phenotypes were characterized further viz. AR9 and AR18, in which GBP2 and GBP1 were respectively the predominant glucose-binding proteins When single colonies of strains AR9 and AR18 were grown in continuous culture under glucose limitation (0.045 h$^{-1}$) they exhibited glucose uptake rates of 63 and 74 nmol min$^{-1}$ (mg dry wt)$^{-1}$ respectively as soon as the steady state was attained. SDS-PAGE of whole cell suspensions, and FPLC analysis of shock fluids, prepared from the two strains revealed that they had retained the capacity to produce both of the glucose-binding proteins, albeit at vastly different amounts; GBP2 was the major glucose-binding protein produced by strain AR9 and GBP1 was the most abundant in strain AR18, but both strains produced similar amounts of BP3 (see also FIG. 3). This finding suggested that prolonged growth under glucose limitation had resulted in the selection of strains of *A. radiobacter* in which either (but not both) of the glucose-binding proteins were further de-repressed relative to the parent organism.

Unlabelled glucose analogues that reduced the extent of binding of [$^{14}$C]glucose to GBP1 in vitro (Table 1) also diminished the rate of uptake of glucose by strain AR18 (Table 2) in the same rank order of potency (i.e. D-galactose=6-chloro-6-deoxy-D-glucose>D-fucose>6-deoxy-D-glucose>D-xylose). By comparison, the uptake of [$^{14}$C]glucose by strain AR9 was much less sensitive to inhibition by a given analogue, the only exception being 6-deoxy-D-glucose (Table 2) which was also more effective at preventing glucose from binding to GBP2 than to GBP1 in vitro (Table 1). The results of these competition experiments were entirely consistent with the proposal that most of the glucose taken up by strain AR18 is transported via system involving GBP1, whilst strain AR9 uses predominantly GBP2. Indeed, the results obtained with D-galactose, which abolished the binding of glucose to GBP1 in vitro but had no effect with GBP2 (Table 1), suggested that approximately 90% of the glucose taken up by strain AR18 was transported via GBP1 compared with only 25% for strain AR9 (Table 2). 2-Deoxy-D-glucose reduced the rate of glucose uptake to a relatively small extent with both strains but had no effect on the binding of glucose to GBP1 or GBP2 in vitro, thus suggesting either that the organism may possess and additional, low-activity glucose uptake system that is as yet uncharacterized or that there are slight differences between binding and tranposrt effects.

METHODS (2)

*A. radiobacter* strains AR9 and AR18 were stored in 20% (v/v) glycerol at −70° C.

Glucose-limited growth was carried out as described above. In order to achieve ammonia-limited growth (steady-state biomass density=1.1 gl$^{-1}$) the input concentration of ammonium sulfate was reduced to 0.5 gl$^{-1}$ and the glucose concentration was increased to 16 gl$^{-1}$ unless stated otherwise. For K$^+$-limited growth (steady-state biomass density=1.1 g dry wt l$^{-1}$) glucose was added to the culture at an input concentration of 15 gl$^{-1}$, KH$_2$PO$_4$ was replaced by Na$_2$HPO$_4$ plus 0.2 mM KCl and the pH of the culture was maintained at 7.0 using 2M NaOH instead of KOH.

Preparation of cell suspensions. Cell suspensions were prepared from glucose-limited cultures using 20 mM HEPES/KOH buffer, pH 7.0 as described above. Samples from ammonia- and potassium-limited cultures were diluted by an appropriate factor using 20 mM HEPES, pH 7.0, before the initial centrifugation to facilitate separation of the cells from the highly viscous succinoglucan exopolysaccharide present in the supernatant. Succinoglucan was precipitated using propan-2-ol (4 vol. propan-2-ol:1 vol. supernatant), collected using a glass rod, and then dried to constant weight at 100° C.

Measurement of succinoglucan production by batch cultures.

*A. radiobacter* was grown at 30° C. in baffled flasks containing 130 ml minimal medium (Linton et al., 1987) supplemented with ammonium sulphate (0.22 gl$^{-1}$) and either glucose or sucrose (8 gl$^{-1}$) Following inoculation, cells grew logarithmically until the ammonia was exhausted (cell density=0.5 g dry wt l$^{-1}$) and thereafter produced succinoglucan. The culture was harvested 24 hours after inoculation and the concentration of succinoglucan was measured as described above. The pH was maintained at 6.8 - 0.2 by the intermittant addition of 2M KOH.

Measurement of rates of glucose utilization and succinoglucan production by cell suspensions. Suspensions of *A. radiobacter* (3 mg dry wt cells in electrode vessel (Rank Bros.). The suspension was mixed continuously using a magnetic stirrer so as to ensure that the dissolved oxygen concentration exceeded 50% saturation. Incubations were started by adding D-[U-$^{14}$C]glucose [0.5 mCi mmol$^{-1}$ (18.5 MBq mmol$^{-1}$); 2.25 uCi (0.083 MBq)] to give a final concentration of 1.5 mM. Samples (0.3 ml) of the cell suspension were removed at intervals over a period of 45 min, the cells were pelleted using centrifugation (13000g for 1 min) and a sample (25 ul) of each supernatant was loaded onto Whatman DE 81 chromatography paper. The papers were developed using 20 mM HEPES, pH 7.0 and then dried at 100° C. for 15 min (glucose migrated with the solvent front and succinoglucan remained at the origin using this system). Regions of the chromatograms that contained glucose and succinoglucan were located precisely using autoradiography, then cut out, immersed in 3 ml Fisofluor 3 (Fisons Ltd.) and counted using a Hewlett Packard Tri-Carb liquid scintillation counter (50–60% efficiency).

Estimation of flux control coefficients for glucose transport on respiration and succinoglucan production. The rates of glucose uptake and respiration by suspensions of *A. radiobacter* strain AR18 were measured as described previously (Cornish et al., 1987; and above).

Assays were started by adding D-glucose to give a final concentration of 250M and the rate of glucose uptake was varied using appropriate concentrations (0–1.5 mM) of 6-chloro-6-deoxy-D-glucose to inhibit the glucose transport system. Rates of glucose uptake and respiration were measured respectively over the first 1 min and 2 min after adding glucose. Rates of glucose utilization and succinoglucan production by cell suspensions were measured as described above except that incubations were started by adding D-[U-$^{14}$C]glucose [0.5 mCi mmol$^{-14}$ (18.5 MBq mmol$^{-1}$; 2.25 Ci (0.083 MBq) to give a final concentration of 1 mM and measurements were carried out over a period of 12 min in the presence and absence of 6-chloro-6-deoxy-D-glucose (0–2 mM). Flux control coefficients were determined by plotting the normalized rates of glucose uptake, respiration and succinoglucan production versus the inhibitor concentration using the method of Walter et al (1987).

Assay of enzyme activities in cell-free extracts. Cell-free extracts were prepared as described previously (Cornish et al., 1987). The following enzymes were assayed at 30° C. using modifications of established procedures (given in parentheses): hexokinase, phosphoglucomutase, phosphofructokinase and UDP-glucose pyrophosphorylase (Bergmeyer, Methods of Enzymatic Analysis Vol. I, 1974); glucose-6-phosphate dehydrogenase and 6-phosphogluconate dehydrogenase (NADP$^+$-linked) (Beardsmore et al., 1982); 6-phosphogluconate hydratase plus 2-keto-3-deoxy-6-phosphogluconate aldolase (Wood, 1971); and UDP-galactose-4-epimerase (Maxwell et al., 1962).

Other methods. Purification of periplasmic glucose-binding proteins, SDS-PAGE and measurement of substrate binding using equilibrium dialysis were carried out as described above.

Presentation of data. Where appropriate, values have been given as the mean ±SEM with the number of determinations in parentheses.

Chemicals. D-[U-$^{14}$C]glucose [270 mCi mmol$^{-1}$) (10 GBq mmol$^{-1}$)] was purchased from Amersham International. 6-Chloro-6-deoxy-D-glucose was obtained from Sigma. Other reagents were purchased from Fisons Ltd. and were of the highest grade available.

RESULTS (2)

*A. radiobacter* strain AR9 produced succinoglucan at the same rate as the parent organism during ammonia-limited growth, and the glucose uptake systems of the two strains were both substantially repressed (Table 3). By contrast, the glucose uptake system of strain AR18 was repressed much less strongly and this strain produced succinoglucan at a significantly higher rate than either the parent organism or strain AR9. These observations suggested that the glucose transport system involving GBP1 was indeed less sensitive to repression than that involving GBP2, and provided further evidence that the activity of the glucose uptake system was an important factor in determining the rate of succinoglucan production. Unlabelled D-galactose, which competes effectively with glucose for GBP1 but not GBP2 in vitro (see above), reduced the rates of glucose uptake by strains AR9 and AR18 by approximately 50% and 95% respectively when it was added to cell suspensions at a forty-fold molar excess over [$^{14}$C]glucose, confirming that strain AR18 takes up glucose using predominantly GBP1 during ammonia-limited growth whereas strain AR9 apparently uses GBP1 and GBP2 to a similar extent.

*A. radiobacter* strain AR18 also produced succinoglucan at significantly higher rates than either strain AR9 or the parent organism during batch culture experiments in which glucose was used as the carbon source (Table 4), but the three strains produced succinoglucan at similar rates when glucose was replaced by sucrose. These results therefore further supported the view that an enzyme involved specifically with glucose uptake or metabolism had becom de-repressed in strain AR18 relative to the other strains, thereby enabling it to convert glucose into succinoglucan at a higher rate.

The relationship between the rate of succinoglucan production and the activity of the glucose uptake system of *A. radiobacter* grown under ammonia limitation (D=0.045 h$^{-1}$).

Figure 7:
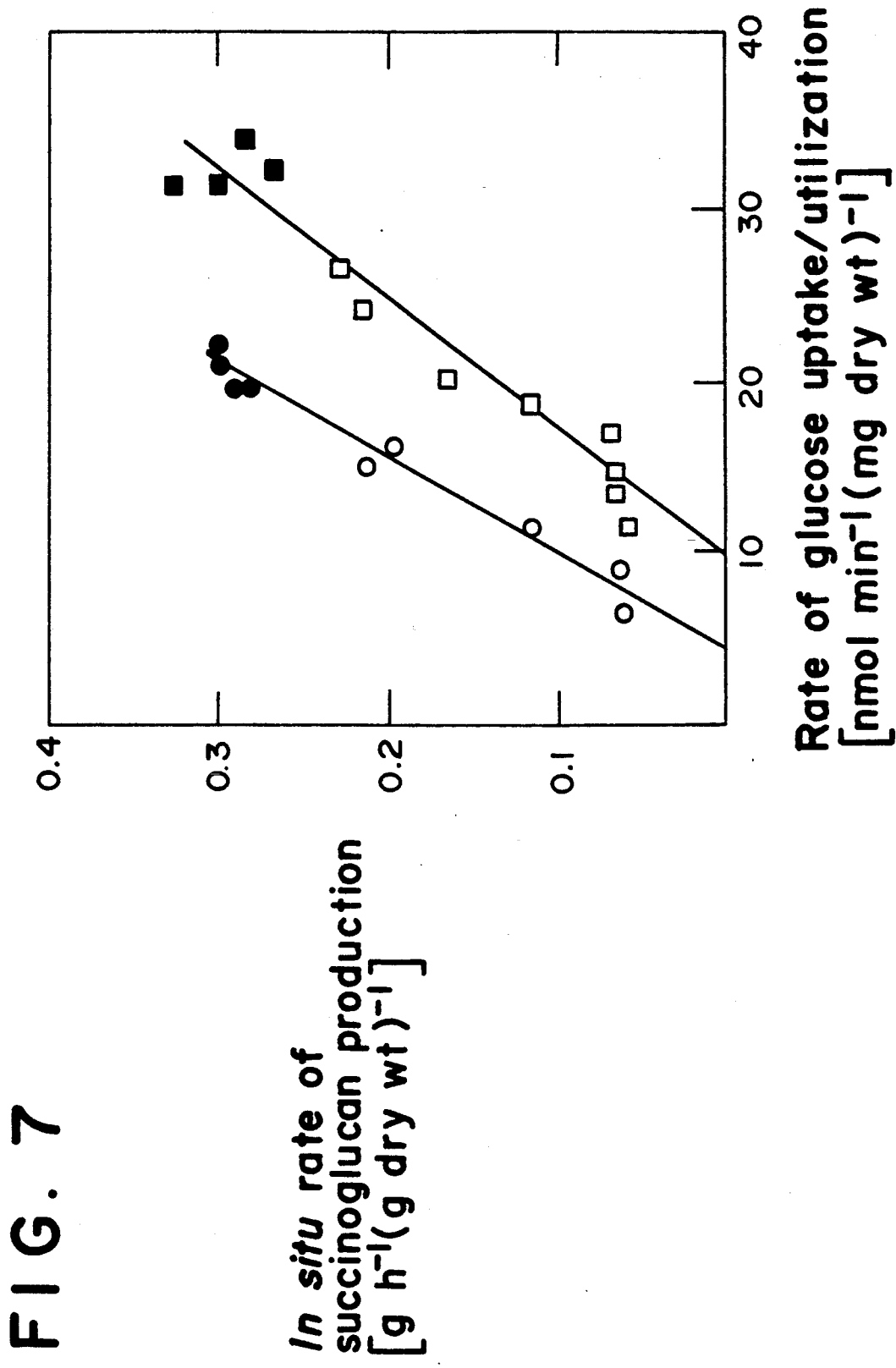
FIG. 7 shows rate of glucose uptake and utilisation and rate of succinoglucan production by *A. radiobacter* strains AR 9 and AR 18 grown in continuous culture under ammonia limitation.

It may be noted that *A. radiobacter* produced succinoglucan at progressively lower rates during prolonged growth under ammonia limitation (D=0.045 h$^{-1}$) and the same phenomenon was observed in the present work with strain AR9. The rate at which this strain produced succinoglucan decreased slowly from 0.20 to 0.16 gh$^{-1}$ (g dry wt)$^{-1}$ during the first 30 generations of ammonia-limited growth, then more rapidly to a value of 0.07 g h$^{-1}$ (g dry wt)$^{-1}$ over the next 16 generations, but thereafter remained constant. This decay in the rate of succinoglucan production was not due to the emergence of mutants that had completely lost the capacity to produce exopolysaccharide (e.g. as a result of a lesion in the biosynthetic pathway) since only mucoid colonies were observed when a samples were removed from the decayed culture and plated on to a solid medium that supported succionoglucan production. Neither was it due to the repression of enzymes involved in the early stages of glucose metabolism or in the production of succinoglucan precursors since the activities of enzymes involved in catabolism remained constant throughout the entire period of ammonia-limited growth. There was, however, a strong correlation between the rates at which strain AR9 produced succinoglucan and transported glucose, and this relationship also held true when succinoglucan was being produced by strain AR18 at the much higher, undecayed rate of 0.3 g h$^{-1}$ (g dry wt)$^{-1}$ (FIG. 7). The data therefore indicated that the rate at which the organism produced succionoglucan was determined primarily by the activity of the glucose uptake system. It remains to be established, however, why the rate of succinoglucan production diminished during prolonged growth under ammonia-limitation, but a plausible explanation might be that the glucose uptake systems become progressively repressed (e.g. by a reversal of the process that leads to their de-repression during glucose-limited growth; see above).

It was notable that the plots in FIG. 7 did not pass through the origin but intercepted the abscissa. The intercept value for the rate of glucose utilization was similar to the rate at which *A. radiobacter* consumed glucose in situ [9 nmol min$^{-1}$ (mg dry wt)$^{-1}$] during glucose-limited growth. The intercept value for the rate of glucose uptake was lower than this, but it should be remembered that the measured rates of glucose uptake were lower than the actual rates of glucose utilisation because a significant proportion (up to 40%) of the label taken up by the cells was lost due to further metabolism. These observations clearly support the proposal that *A.*

*radiobacter* produced succinoglucan during ammonia-limited growth in order to dispose of any transported glucose that was surplus to the requirement for growth.

TABLE 1

Effect of glucose analogues on the binding of [$^{14}$C]glucose to GBP1 and GBP2.
Binding of [$^{14}$C]glucose to the pure binding proteins in the presence and absence of unlabelled sugars was measured using equilibrium dialysis as described in the Methods.

| Analogue | [$^{14}$C]glucose bound | |
|---|---|---|
| | GBP1 | GBP2 |
| | (% control value) | |
| none (control) | 100 | 100 |
| alpha-1-O-methyl-D-glucose | 99 | 104 |
| 3-O-methyl-D-glucose | 100 | 103 |
| 2-deoxy-D-glucose | 96 | 98 |
| D-fucose | 31 | 99 |
| D-galactose | 2 | 99 |
| 6-deoxy-D-glucose | 51 | 0 |
| 6-chloro-6-deoxy-D-glucose | 0 | 60 |
| D-xylose | 72 | 2 |
| D-glucose | 4 | 4 |

TABLE 2

Effect of glucose analogues on the uptake of [$^{14}$C]glucose by strains of *A. radiobacter* grown in continuous culture under glucose limitation (D = 0.045 h$^{-1}$).
Strains AR18 and AR9, which contained high concentrations of GBP1 and GBP2 respectively, were isolated from a glucose-limited culture of *A. radiobacter* as described above. Uptake of [$^{14}$C]glucose (250M) was measured as described in the Methods. Unlabelled sugars (10 mM) were present in the assays as indicated. The uptake rates measured for control incubations [nmol min$^{-1}$ (mg dry wt)$^{-1}$] were as follows: AR18, 72; AR9, 63. ND = value not determined.

| | Glucose uptake rate | |
|---|---|---|
| | strain AR18 | strain AR9 |
| Addition to assay | (% control value) | |
| none (control) | 100 | 100 |
| alpha-1-O-methyl-D-glucose | 111 | 99 |
| 3-O-methyl-D-glucose | 111 | 99 |
| 2-deoxy-D-glucose | 93 | 71 |
| D-fucose | 18 | 68 |
| D-galactose | 8 | 75 |
| 6-deoxy-D-glucose | 27 | 11 |
| 6-chloro-6-deoxy-D-glucose | 8 | 33 |
| D-xylose | 64 | ND |
| D-glucose | 4 | 4 |

TABLE 3

Rates of glucose uptake and succinoglucan production by various strains of *A. radiobacter* grown in continuous culture under ammonia-limitation (D = 0.045 h$^{-1}$)
The rate of glucose uptake by washed suspensions and of succinoglucan production by growing cultures were measured as described in the Methods. The results shown for strains AR9 and AR18 refer to individual experiments.

| Strain | glucose uptake rate [nmol min$^{-1}$ (mg dry wt)$^{-1}$] | in situ rate of succinoglucan production [h$^{-1}$ (g dry wt)$^{-1}$] | % |
|---|---|---|---|
| Parent | 10 ± 1 (3) | 0.21 ± 0.01 (3) | 100 |
| AR9 | 14 ± 1 (4) | 0.20 ± 0.01 (5) | 97 |
| AR9 | 12 (2) | 0.21 ± 0.02 (4) | 102 |
| AR18 | 19 ± 1 (3) | 0.29 ± 0.01 (4) | 141 |
| AR18 | 21 ± 1 (3) | 0.31 ± 0.02 (4) | 150 |

TABLE 3-continued

| | | | |
|---|---|---|---|
| AR18 | 19 (1) | 0.29 ± 0.02 (3) | 141 |

TABLE 4

The production of succinoglucan by various strains of *A. radiobacter* during batch culture with glucose or sucrose as carbon source.
The various strains were inoculated into a medium containing a low concentration of ammonium sulphate (0.22 gl$^{-1}$) and grew logarithmically until they became starved of ammonia [final cell density = 0.5 g dry wt l$^{-1}$) and thereafter produced succinoglucan. The cultures were harvested 24 hours after inoculation and the rates of succinoglucan production were determined as described in the Methods.

| Strain | carbon source | in situ rate of succinoglucan following ammonia exhaustion | |
|---|---|---|---|
| | | [g h- (g dry wt)$^{-1}$] | (%) |
| Parent | glucose | 0.20 ± 0.01 (3) | 100 |
| | sucrose | 0.19 ± 0.01 (3) | 95 |
| AR9 | glucose | 0.20 ± 0.01 (3) | 100 |
| | sucrose | 0.16 ± 0.01 (3) | 80 |
| AR18 | glucose | 0.29 ± 0.02 (4) | 145 |
| | sucrose | 0.19 ± 0.01 (4) | 95 |

The figures in the accompanying drawings will now be described in greater detail.

FIG. 1. Purification of three major periplasmic proteins from whole cells of *A. radiobacter* grown in continuous culture under glucose limitation (D=0.045 h$^{-1}$) a). SDS-PAGE gels showing the relative concentration of the three proteins following growth under glucose and ammonia limitation (G=glucose, A=ammonia). b). Partial release of the proteins by osmotic shock (WC=whole cells, SC=shocked cells, SF=shock fluid). c). SDS-PAGE gel showing the individual proteins purified from the shock fluid using anion exchange FPLC (see Methods above).

FIG. 2. Scatchard plots for the binding of glucose to two proteins released from whole cells of *A. radiobacter* by osmotic shock. The binding of $^{14}$C-glucose to pure samples of GBP1 (M$_r$=36500) (●) and GBP2 (M$_r$=33500) (0) was measured using equilibrium dialysis as described in the Methods. K$_D$ values were obtained from the slopes using the method of Scatchard (1949). The intercepts on the abscissa give the stoichiometry of binding.

FIG. 3. SDS-PAGE gel showing the variations in the concentrations of GBP1, GBP2 and BP3 in whole cells of *A. radiobacter* taken from several different cultures growing under glucose limitation (0.045 h$^{-1}$). Tracks labelled AR9 and AR18 show the polypeptide profiles of two new strains of *A. radiobacter*, the isolation of which is described above.

FIG. 4. The relationship between the glucose uptake capacity of whole cells of *A. radiobacter* grown in continuous culture under glucose limitation (D=0.045 h$^{-1}$) and the concentrations of GBP1, GBP2 and BP3. Samples were withdrawn from different cultures and the glucose uptake capacity of the cells were measured using [$^{14}$C]-glucose. Cellular proteins were then separated using SDS-PAGE, and the concentrations of GBP1, GBP2 and BP3 were determined using microdensitometry and expressed as a percentage of the total cell protein. The abundance of GBP1plus GBP2 (0) and BP3 (●) was then plotted against the glucose uptake rate.

FIG. 5. SDS-PAGE gel showing changes in the concentrations of GBP1 and GBP2 following prolonged growth of *A. radiobacter* under glucose limitation (D =0.045 h$^{-1}$). Samples were withdrawn from the culture at intervals and the polypeptide profiles of the cells were examined using SDS-PAGE. Numbers above individual tracks indicate the number of generation times between the onset of glucose limitation and the time of sampling. Glucose uptake rates [nmol min$^{-1}$ (mg dry wt)$^{-1}$] are given below each track.

FIG. 6. SDS-PAGE gel showing strains of *A. radiobacter* having different concentrations of glucose-binding proteins. A sample was withdrawn from a glucose-limited culture of *A. radiobacter* and streaked out onto solid medium. Twenty three colonies were then selected at random and grown overnight in small-scale (3 ml) batch culture. Protein profiles of the individual cultures were then compared using SDS-PAGE, and thirteeen of these are shown. The positions of GBP1, GBP2 and BP3 are indicated. Two distinct phenotypes were distinguished, of which strains AR9 and AR18 are representative.

FIG. 7. Relationship between the rates of glucose uptake and utilisation by washed cells and the rate of succinoglucan production in situ by *A. radiobacter* strains AR9 and AR18 grown in continuous culture under ammonia limitation (D=0.045 h$^{-1}$. Strain AR9 was grown in continuous culture under ammonia limitation for 50 generations, during which time the rate of succinoglucan production decreased substantially (see text). Strain AR18 was grown under the same conditions except that measurements were made within 15 generation times of the ammonia-limited steady state being established. Rates of glucose uptake (○) and utilisation (□) by washed cell suspensions; strain AR9 (open symbols) and strain AR18 (closed symbols).

References given above in terms of author and date are defined as follows:

AMES, G. F.-L. (1986). Bacterial periplasmic transport systems: structure, mechanism, and evolution. *Annual Review of Biochemistry* 55, 397–425.

BEARDSMORE, A. J., APERGHIS, P. N. G. & QUAYLE, J. R. (1982). Characterisation of the assimilatory and dissimilatory pathways of carbon metabolism during growth of *Methylophilus methylotrophus* on methanol. *Journal of General Microbiology* 128, 1423–1439.

BRASS, J. M., EHMANN, U. & BUKAU, B. (1983). Reconstitution of maltose transport in *Escherichia coli*: conditions affecting import of maltose-binding protein into calcium-treated cells of maltose regulon mutants. *Journal of Bacteriology* 155, 97–106.

COLLINS, S. H., JARVIS, A. W., LINDSAY, R. J. & HAMILTON, W. A. (1976). Proton movements coupled to lactage and alanine in *Escherichia coli*: isolation of mutants with altered stoichiometry in alanine transport. *Journal of Bacteriology* 126, 1232–1244.

CORNISH, A., LINTON, J. D. & JONES, C. W. (1987). The effect of growth conditions on the respiratory system of a succinoglucan-producing strain of *Agrobacterium radiobacter*. *Journal of General Microbiology* 133, 2971–2978.

DURHAM, D. R. & PHIBBS, P. V., Jr. (1982). Fractionation and characterization of the phosphoenolpyruvate: fructose 1-phosphotransferase system from *Pseudomonas aeruginosa*. *Journal of Bacteriology* 149, 534–541.

HARDER, W. & DIJKHUIZEN, L. (1983). Physiological responses to nutrient limitation. *Annual Review of Microbiology* 37, 1–23.

HARDER, W, KUENEN, J. G. & MATIN, A. (1977). Microbial selection in continuous culture. *Journal of Applied Bacteriology* 43, 1–24.

HENDERSON, P. J. F. (1986). Active transport of sugars into *Escherichia coli*. In *Carbohydrate Metabolism in Culture Cells*, pp 409–460. Edited by M. J. Morgan. Plenum Press.

HENDERSON, P. J. F. & MACPHERSON, A. J. S. (1986). Assay, genetics, proteins and reconstitution of proton-linked galactose, arabinose and xylose transport systems of *Escherichia coli*. *Methods in Enzymology* 125, 387–429.

LAEMMLI, U. K. (1970). Cleavage of structural proteins during the assembly of the head of bacteriophage T4. *Nature*, London 227, 680–685.

LINTON, J. D., EVANS, M. W., JONES, D. S. & GOULDNEY, D. G. (1987). Exocellular succinoglucan production by *Agrobacterium radiobacter* NCIB 11883. *Journal of General Microbiology* 133, 2961–2969.

LINTON, J. D., WOODARD, S. & GOULDNEY, D. G. (1986). The consequence of stimulating glucose dehydrogenase activity by the addition of PQQ on metabolite production by *Agrobacterium radiobacter* NCIB 11883. *Applied Microbiology and Biotechnology* 25, 357–361.

MAXWELL, E. S., KURAHASHI, K. & KAKAR, H. M. (1962). Enzymes of the Leloir pathway. *Methods in Enzymology* V, 174–190.

MIDGLEY, M. & DAWES, E. A. (1973). The regulation of transport of glucose and methyl alpha-glucoside in *Pseudomonas aeruginosa*. *Biochemical Journal* 132, 141–154.

NEU, H. C. & HEPPEL, L. A. (1965). The release of enzymes from *Escherichia coli* by osmotic shock and during the formation of sphaeroplasts. *Journal of Biological Chemistry* 240, 3685–3692.

POSTMA, P. W. (1986). The bacterial phosphoenolpyruvate: sugar phosphotranferase system of *Eschrichia coli* and *Salmonella typhimurum*. In: *Carbohydrate metabolism in cultured cells*, pp 367–408 Edited by M. J. Morgan. Plenum Press.

QUILTER, J. A. & JONES, C. W. (1984). The organisation of emthanol dehydrogenase and c-type cytochromes on the respiratory memberance of *Methylophilus methylotrophus*. *FEBS Letters* 174, 167–172.

ROBERTS, B. K., MIDGLEY, M. & DAWES, E. A. (1973). The metabolism of 2-oxogluconate by *Pseudomonas aeruginosa*. *Journal of General Microbiology* 78, 319–329.

RUTGERS, M., TEIXERA DE MATTOS, M. J., POSTMA, P. W. & VAN DAM, K. (1987). Establishment of the steady state in glucose-limited chemostat cultures of *Klebsiella pneumoniae*. *Journal of General Microbiology* 133, 445–451.

SCATCHARD, G. (1949). The attractions of proteins for small molecules and ions. *Annals of the New York Academy of Science* 51, 660–672.

STINSON, M. W., COHEN, M. A. & MERRICK, J. M. (1977). Purification and properties of the periplasmic glucose-binding protein of *Pseudomonas aeruginosa*. *Journal of Bacteriology* 131, 672–681.

de VRIES, G. E., VAN BRUSSEL, A. N. & QUISPEL, A. (1982). Mechanism and regulation of glucose transport in *Rhizobium leguminosarum*. *Journal of Bacteriology* 149, 872–879.

WALTER, R. P., MORRIS, J. G. & KELL, D. B. (1987). The roles of osmotic stress and water activity in the phosphotransferase system of *Clostridium pasteurianum*. *Journal of General Microbiology* 133, 259-266.

WEBER, K. & OSBORNE, M. (1975). Proteins and sodium dodecyl sulphate: molecular weight determinations on polyacrylamide gels and related procedures. In *The Proteins I*, 3rd Ed., 179-223, Ed. H. Neurath & R. L. Hill, London, Academic Press.

WHITING, P. H., MIDGELY, M. & DAWES, E. A. (1976). The role of glucose limitation in the regulation of the transport of glucose, gluconate and 2-oxogluconate, and of glucose metabolism in *Pseudomonas aeruginosa*. *Journal of General Microbiology* 92, 304-310.

WOOD, W. A. (1971). Assay of enzymes representative of metabolic pathways. *Methods in Microbiology* 6A 411-424 ed. J. R. Norris & D. W. Ribbons, Acad. Press London.

We claim:

1. A biologically pure culture of *Agrobacterium radiobacter* NCIB 40018.

2. A process for obtaining a microorganism of increased capability of producing an extra-cellular heteropolysaccharide, from a starting microorganism of the species *Agrobacterium radiobacter* having the capability of producing an extra-cellular polysaccharide when grown in the presence of a glucose substrate which is limiting for the production of the extra-cellular polysaccharide and containing two periplasmic glucose-binding proteins, said process comprising the steps of (1) culturing said starting microorganism in a continuous culture containing glucose under limitation and sources of sulfur and nitrogen, to selectively obtain a microorganism protein present in greatest amount where the glucose uptake system is derepressed compared to the starting microorganism and having increased capability of producing the extra-cellular polysaccharide compared to the starting microorganism, (2) selecting said obtained microorganism; the extra-cellular polysaccharide being a succinoglucan heteropolysaccharide comprising glucose and, for each 7 moles of glucose, 0.9-1.2 moles of galactose, and 0.65 to 1.1 moles of pyruvate, together with succinate and acetate in molar proportions, based on 7 moles of glucose, between 0 and 2.

3. A process according to claim 2, which comprises the additional steps of culturing the obtained microorganism to produce extra-cellular heteropolysaccharide and recovering said extra-cellular heteropolysaccharide.

* * * * *

UNITED STATES PATENT AND TRADEMARK OFFICE
CERTIFICATE OF CORRECTION

PATENT NO. : 5,125,099

DATED : June 23, 1992

INVENTOR(S) : Alexander Cornish, et al

It is certified that error appears in the above-identified patent and that said Letters Patent is hereby corrected as shown below:

Claim 2 (column 20, lines 8 and 9), delete "protein present in greatest amount"

Signed and Sealed this

Twenty-fourth Day of August, 1993

Attest:

BRUCE LEHMAN

Attesting Officer

Commissioner of Patents and Trademarks